(12) United States Patent
Lenarsic et al.

(10) Patent No.: US 7,498,433 B2
(45) Date of Patent: Mar. 3, 2009

(54) PROCESS AND INTERMEDIATES FOR THE PREPARATION OF OLANZAPINE

(75) Inventors: Roman Lenarsic, Ljubljana (SI); Rok Zupet, Ljubljana (SI); Milena Benedik, Brusnice (SI); Barbara Mohar, Ljubljana (SI); Anton Štimac, Ljubljana (SI)

(73) Assignee: KRKA, Tovarna Zdravil, D.D., Novo Mesto (SI)

( * ) Notice: Subject to any disclaimer, the term of this patent is extended or adjusted under 35 U.S.C. 154(b) by 588 days.

(21) Appl. No.: 10/541,604

(22) PCT Filed: Jan. 16, 2004

(86) PCT No.: PCT/EP2004/000299

§ 371 (c)(1),
(2), (4) Date: Jul. 7, 2005

(87) PCT Pub. No.: WO2004/065390

PCT Pub. Date: Aug. 5, 2004

(65) Prior Publication Data

US 2006/0040921 A1     Feb. 23, 2006

(30) Foreign Application Priority Data

Jan. 17, 2003  (DE) ................. 103 01 923

(51) Int. Cl.
*C07D 495/04* (2006.01)
*C07D 295/04* (2006.01)
(52) U.S. Cl. ...................... 540/557; 540/567
(58) Field of Classification Search ................ 540/557, 540/567

See application file for complete search history.

(56) References Cited

FOREIGN PATENT DOCUMENTS

| EP | 0454436 | 10/1991 |
|----|---------|---------|
| GB | 1533235 | 11/1978 |

OTHER PUBLICATIONS

Calligaro et al., The synthesis and biological activity of some known and putative metabolites of the atypical antipsychotic agent olanzapine (LY170053), XP-002279427, Bioorganic & Medicinal Chemistry Letters, vol. 7, No. 1, pp. 25-30 (1997).

Gewald et al., 2-Amino-thiophene aus methylenaktiven Nitrilen, Carbonylverbindungen und Shwefel, Chem. Ber. (1996), pp. 94-100.

Karl Gewald, 2-Amino-thiopene aus α-Oxo-mercaptanen und methylenaktiven Nitrilen[2], Chem. Ber. (1965), pp. 3571-3577.

*Primary Examiner*—Brenda L Coleman
(74) *Attorney, Agent, or Firm*—Cohen Pontani Lieberman & Pavane LLP

(57) ABSTRACT

The invention provides an improved process for preparing Olanzapine as well as intermediates therefor.

14 Claims, No Drawings

PROCESS AND INTERMEDIATES FOR THE PREPARATION OF OLANZAPINE

PRIORITY CLAIM

This is a U.S. national stage of application No. PCT/EP2004/000299, filed on Jan. 16, 2004, which claimed priority from Germany Patent Application No. 10301923.5 filed on Jan. 17, 2003.

The invention belongs to the field of organic chemistry and relates to a new process and intermediates for the manufacture of a compound having the following formula I:

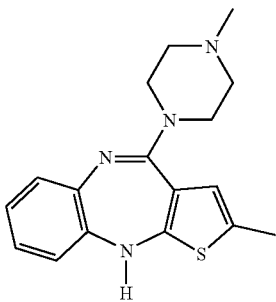

i.e. 2-methyl-4-(4-methyl-1-piperazinyl)-10H-thieno[2,3-b]-[1,5]benzodiazepine (hereinafter referred to by its generic name "Olanzapine")

Olanzapine is a serotonin (5-HT$_2$) and dopamine (D$_1$/D$_2$) receptor antagonist with anticholinergic activity. It is useful in treating psychotic conditions such as schizophrenia, schizophreniform disorders, acute mania, states of mild anxiety and psychosis.

Heretofore, only a few processes for the manufacture of Olanzapine have become known.

British patent GB 1,533,235 discloses a series of thieno[1,5]-benzodiazepine derivatives which are represented by the following generic formula:

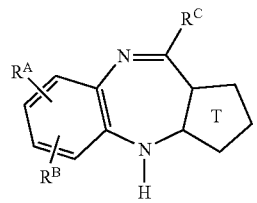

wherein R$^A$ and R$^B$ represent various substituents, e.g. hydrogen, R$^C$ represents amine substituents, e.g. 4-methylpiperazinyl, and T represents thiophene rings fused to the [1,5]-benzodiazepine ring. An example of these derivatives is 2-methyl-10H-thieno-[2,3-b] [1,5] benzodiazepine. These benzodiazepine derivatives are prepared by reacting a suitable precursor with an amine HR$^C$ so as to introduce the amine substituent R$^C$ in the molecule.

Olanzapine and its synthesis were specifically disclosed in EP 0 454 436 A1. This application discloses two synthetic paths, which are depicted in scheme 1 below.

Both paths start with a Gewald reaction to form appropriately substituted 2-amino-thiophenes (a). This type of reaction is described in *Chem. Ber.* 1965, 98, 3571-3577; *Chem. Ber.* 1966, 99, 94-100. The second step involves the reaction of 2-aminothiophene with 2-nitro-1-fluorobenzene (b), to give a 2-(2-nitro-anilino)thiophene.

According to the first reaction path, this thiophene is then (c) reduced and cyclised to a benzodiazepine-4-amine hydrochloride. Replacement of the amine group by 1-methylpiperazine (d) leads to the desired Olanzapine.

In the second reaction path, the thiophene is catalytically hydrogenated to an amino-ester (e), which is then transformed into an amino-amide (f), and this amino-amide is subsequently cyclised (g) to give Olanzapine. This second approach requires chromatographic purification in each step, because the reactions lack selectivity and because the products could not be obtained by precipitation.

Scheme 1:

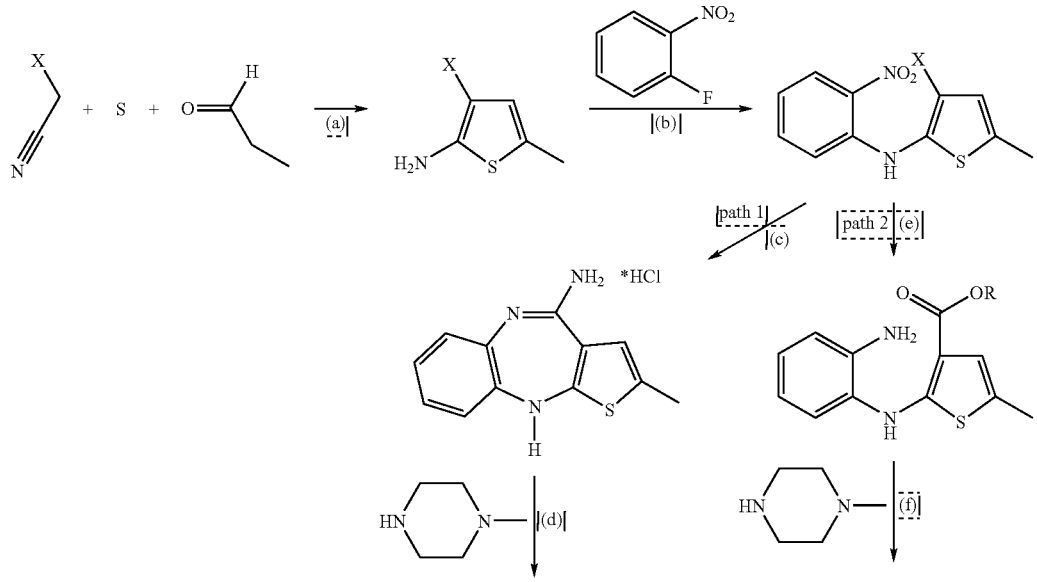

-continued

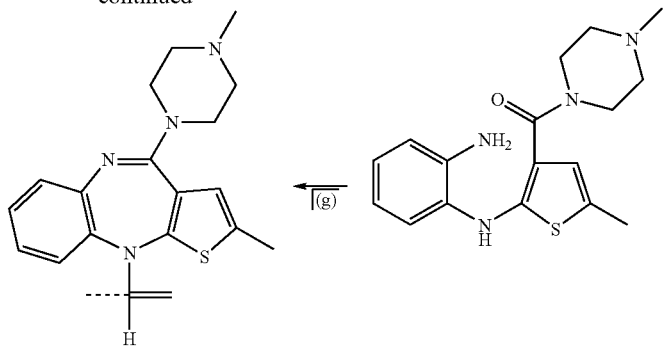

In path 1, X is CN and in path 2, X is COOR, e.g. COOC$_2$H$_5$.

The reagents used in the respective steps of the reactions were as follows: (a) Et$_3$N, DMF; (b) NaH, THF; (c) SnCl$_2$ HCl; (d) DMSO, toluene; (e) H$_2$, Pd/C, EtOH-EtOAc; (f) TiCl$_4$, anisole; (g) TiCl$_4$, anisole.

Besides the already mentioned requirement for chromatographic purification in early steps, causing high costs, low yields and substantial amounts of waste products, both paths have some further drawbacks. They provide only low yields, e.g. in the case of path 2 with X being COOC$_2$H$_5$ the yield of the fist step is only 42.5% as is reported in *J. Heterocyclic Chem.* 36, 1999, 333-345. Other drawbacks are that expensive compounds such as Pd have to be used as well as compounds that are toxic and not acceptable from an environmental point of view, like DMF, TiCl$_4$ or SnCl$_2$.

Thus, there exists a need for an improved process which overcomes these drawbacks.

This object is surprisingly solved by the process for the manufacture of Olanzapine according to claims 1 to 5. The invention is also directed to the compounds according to claims 6 to 9 as well as to their use according to claim 10.

The process according to the invention for the manufacture of Olanzapine is characterized by converting a compound of the following formula II or a salt thereof

II

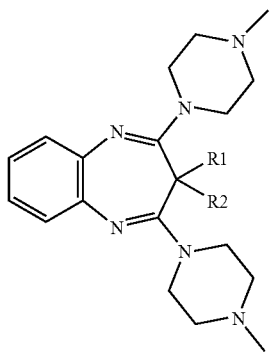

in which
(i) R1 and R2 together form =CH—CH$_2$—CH$_3$, or
(ii) R1 and R2 are both H, or
(iii) R1 is H and R2 is —CH(R3)—CH$_2$—CH$_3$, wherein R3 is a leaving group, that can be eliminated together with R1 to result in R1 and R2 together forming =CH—CH$_2$—CH$_3$, to give Olanzapine or a salt thereof.

In the case of (i) the compound to be converted is the propylidene-diazepine of the following formula III:

III

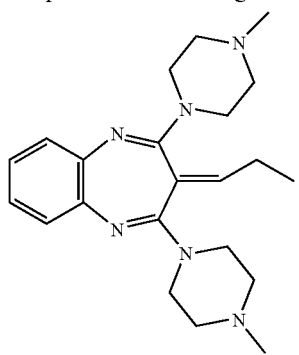

or a salt thereof.

In the case of (ii) the compound to be converted is the diazepine of the following formula IV:

IV

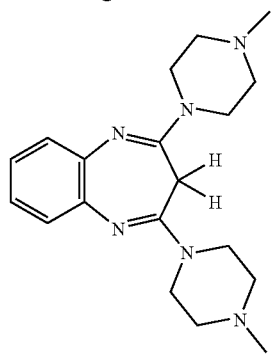

or a salt thereof.

In the case of (iii) the compound to be converted is the diazepine-derivative bearing a leaving group R3, as is shown in the following formula V:

V

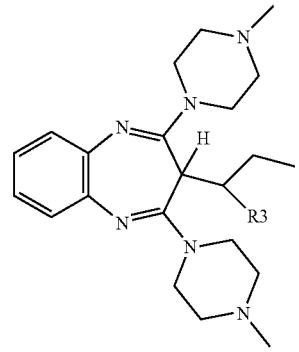

or a salt thereof.

A preferred leaving group R3 is —OR4.

R4 can preferably be H, so that the leaving group R3 is preferably an alkohol group. In such a case the compound to be converted is the diazepine-alcohol of the following formula VI:

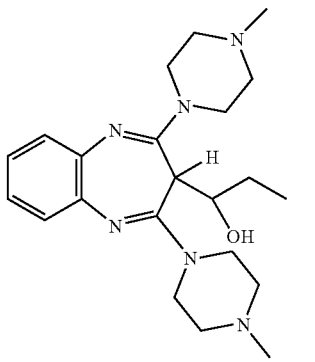

VI or a salt thereof.

R4 can also be selected from the group of acyl, sulfonyl, preferably trifluoroacetyl and methane sulfonyl, so that the leaving group R3 is an ester group, and the compound to be converted is the benzodiazepine-ester of the following formula VII:

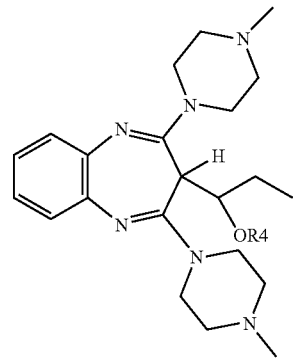

VII or a salt thereof with R4 being preferably selected from the group of acyl, sulfonyl, and with R4 most preferably being trifluoroacetyl or methane sulfonyl.

In a particularly preferred embodiment of the process according to the invention, R1 and R2 together form =CH—CH$_2$—CH$_3$ and the conversion is performed by reacting the compound of formula II with a source of sulfur.

Particularly preferred embodiments of the process according to this invention are depicted in scheme 2, using the preferred precursors of the invention.

Scheme 2:

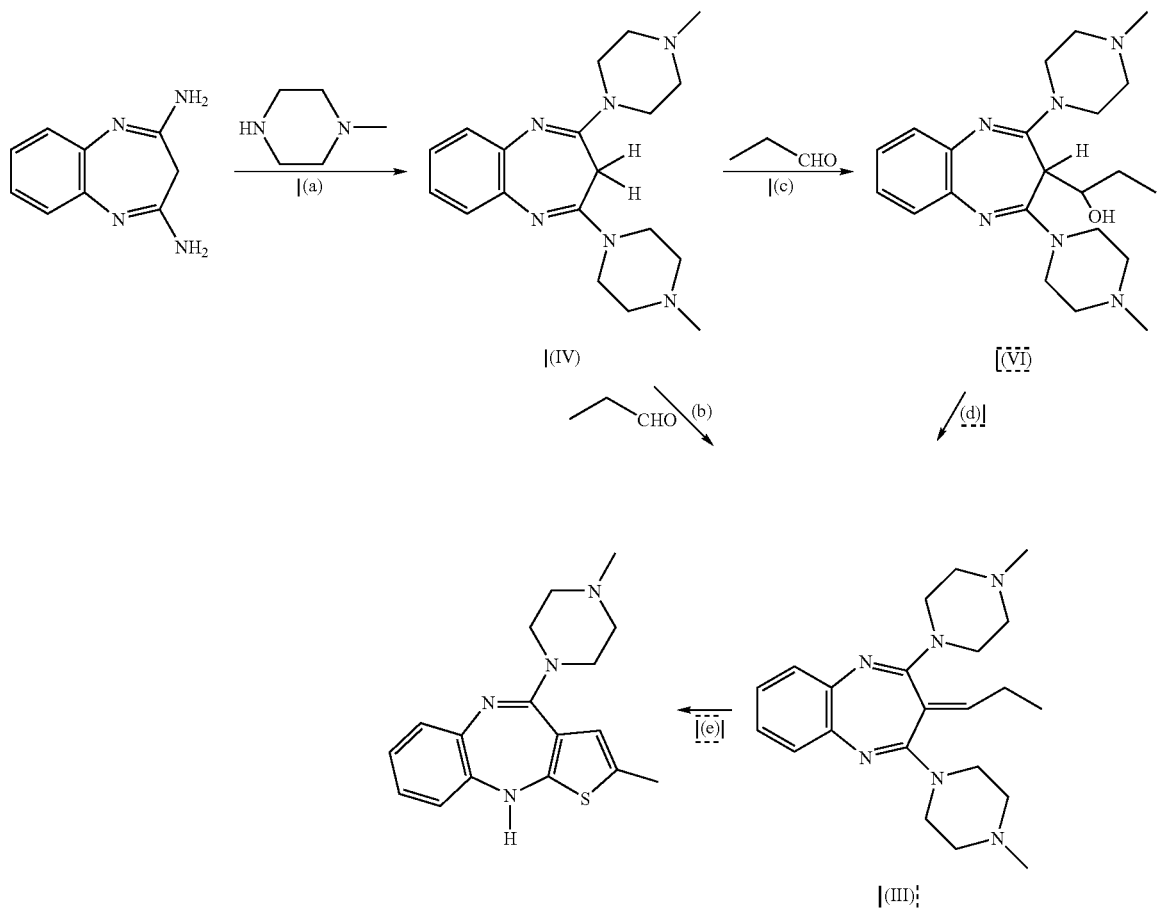

The reagents used in the respective steps are preferably as follows:
(a) Toluene, DMSO; (b) 1. LDA, THF, 2. (CF$_3$CO)$_2$O, NaOH; (c) LDA, THF; (d) (CF$_3$CO)$_2$O, NaOH, THF; (e) [S], R$^1$NR$^2$R$^2$ or AHB or AH.

Besides the advantage of the high yields in the synthesis, the use of symmetrical intermediates according to the present invention is particularly advantageous because the possibility of obtaining undesired regioisomeres is exluded.

Thus, in a first preferred aspect of the invention Olanzapine can be produced in a reaction (e) of the propylidene-benzodiazepine of formula, III with a source of sulphur [S], preferably elementary sulphur or sodium polysulphide, which is usually base mediated. An appropriate base can be chosen among secondary or tertiary alkylamines of formula R$^1$NR$^2$R$^2$, in which R$^1$ is H or R$^2$, and R$^2$ is a C$_1$- to C$_5$-alkyl or cyclic amine such as morpholine, piperidine, piperazine or 1-methyl-piperazine. Preferably the base is chosen from tertiary alkyl-amines and the most preferable base is triethylamine. Acceptable solvents for the reaction are N-methylimidazole, dimethyl sulfoxide (DMSO), C$_1$- to C$_5$-aliphatic alcohols, alcoholamines, diols, polyols or mixtures thereof, preferably mixtures of dimethyl sulfoxide and alcohols. An appropriate reaction temperature range is from room temperature to the boiling point of the reaction mixture, preferably from 50° C. to 150° C. and most preferably is a reaction temperature of about 100° C.

The reaction can also be mediated with a salt AHB. This salt is composed of an acid AH and an amine B. The acid AH can be chosen among organic or anorganic acids. Preferred are organic carboxylic or sulfonic acids, such as acetic acid, trifluoroacetic acid, benzoic acid, 4-nitrobenoic acid, 4-chlorobenzoic acid, methanesulfonic acid, trifluoromethanesulfonic acid, benzenesulfonic acid or p-toluenesulfonic acid and most preferred are p-toluenesulfonic acid or methanesulfonic acid. The amine B can be chosen among secondary or tertiary aliphatic or aromatic amines. Preferred aromatic amines are pyridine picoline, lutidine, quinoline, 2-methylquinoline or 1-methylimidazole and most preferred are pyridine or quinoline. Either part of the salt AHB can be polymer bound. Acceptable solvents for the reaction are high boiling point solvents. They can be hydrocarbons, ethers, esters, nitriles or alcohols or mixtures thereof. Preferred are aromatic ethers, esters, or nitriles, such as anisole, dimethoxybenzene, diphenyl ether, methyl benzoate, ethyl benzoate and benzonitrile and most preferred is benzonitrile. An appropriate reaction temperature range is from 80° C. to 220° C., preferably from 100° C. to 180° C. and most preferred is a reaction temperature of about 140° C.

The propylidene-benzodiazepine of formula III can preferably be synthesised via step (b) from the benzodiazepine of formula IV. In a preferred embodiment the benzodiazepine IV is firstly transformed to an alkali salt using strong bases such as alkali amides, alkali alkyls or alkali silazanes. Preferably lithium diisopropylamide (LDA) or butyl-lithium is used and most preferably lithium diisopropylamide is used. In an addition reaction of the alkali salt of the benzodiazepine IV to propionaldehyde the benzodiazepine-alcoholate of the alcohol of formula VI is formed. The solvent for this reaction should be inert to strong bases and it is in particular chosen from ethers or aromatic hydrocarbons. Water miscible ethers are preferred, with the most preferable solvent being THF. Usual reaction temperatures range from –50° C. to room temperature, preferably from –30° C. to 0° C. The benzodiazepine-alcoholate is than transformed to a benzodiazepine-ester of formula VII, in which R4 is in particular selected from the group of acyl or sulfonyl, preferably acetyl trifluoroacetyl or methane sulfonyl, with trifluoroacetyl being most preferred. The elimination of said ester group to produce the propylidene-benzodiazepine of formula III is accomplished by adding of an aqueous solution of alkali hydroxide salts such as lithium hydroxide, sodium hydroxide or potassium hydroxide and preferably is an aqueous solution of sodium hydroxide. When the organic solvent is immiscible with water, the reaction can be catalysed with quarternary ammonium salts, such as tetraalkylammonium chlorides, bromides, fluorides, hydroxides or cyanides, wherein "alkyl" represents groups having 1 to 8 carbon atoms. Preferably the reaction is catalysed with tetrabutylammonium bromide or hydroxide and most preferably with tetrabutylammonium bromide. It is most preferable that the sequence of these reactions is conducted as a one pot reaction.

Alternatively, the propylidene-diazepine of formula III can be prepared via step (d) starting from the benzodiazepine-alcohol of formula VI. The procedure is similar to the second part of step (b). The benzodiazepine-alcohol is first transformed to a diazepine-ester of formula VII, in which R4 is in particular selected from the group of acyl or sulfonyl, preferably acetyl, trifluoroacetyl or methane sulfonyl, with trifluoroacetyl being most preferred. The elimination of the ester group to produce the propylidene-benzodiazepine of formula III is preferably carried out in a one or two phase solvent system. The organic solvent can be chosen from ethers, halogenated hydrocarbons or aromatic or aliphatic hydrocarbons and is preferably chosen from tetrahydrofuran, dichloromethane or toluene, with the most preferable solvent being tetrahydrofuran. The second solvent can be an aqueous solution of alkali hydroxide salts such as lithium hydroxide, sodium hydroxide, or potassium hydroxide and preferably is an aqueous solution of sodium hydroxide. In case of a two phase solvent system, the reaction can be catalysed with quarternary ammonium salts such as tetraalkylammonium chlorides, bromides, fluorides, hydroxides or cyanides, wherein "alkyl" represents groups having 1 to 8 carbon atoms. Preferably the reaction is catalysed with tetrabutylammonium bromide or hydroxide and most preferably with tetrabutylammonium bromide. It is most preferable that esterification and subsequent elimination of the resulting ester group are conducted as a one pot reaction.

The benzodiazepine-alcohol of formula VI is preferably obtained via step (c) in an addition reaction of an alkali salt of the benzodiazepine of formula IV to propionaldehyde. The alkali salt can be prepared using strong bases such as alkali amides, alkali alkyls or alkali silazanes. Preferably lithium diisopropylamide (LDA) or butyl-lithium is used and most preferably lithium diisopropylamide is used. Due to this possible use of strong bases the benzodiazepine-alcohol of formula VI can also be present in its deprotonized form, i.e. the corresponding benzodiazepine-alcoholate is present. The solvent for this reaction should be inert to strong bases and is in particular chosen from ethers or aromatic hydrocarbons. Ethers are preferred, with the most preferable solvent being THF. Usual reaction temperatures range from –50° C. to room temperature, preferably from –30° C. to 0° C.

The benzodiazepine of formula IV can be synthesised by reacting 3H-[1,5]benzodiazepine-2,4-diamine (*J. Chem. Soc., Chem. Commun.* 1973, 367-368) and 1-methylpiperazine. The reaction can be carried out in a mixture of solvents comprising toluene and dimethyl sulfoxide. The reaction temperature may vary from 60° C. to 180° C., preferably from 90° C. to 150° C. and is most preferably about 120° C.

The compounds according to formulae III to VII mentioned hereinbefore or salts thereof as well as their use for the manufacture of Olanzapine are further objects of the invention.

By the term "or salts thereof" is meant that the compound can not only be present in the form as is shown by formulae I to VII but can also be present in the form of a salt e.g. a salt formed of an organic or inorganic base and an acidic part of the compound such as the alcohol group or a salt formed of an organic or inorganic acid and a basic part of the compound such as the amino-groups. The conversion of one of the substances claimed into its salt or back into the form as is shown by formulae I to VII is within the scope of the invention. This also applies, when this conversion is performed as part of another reaction.

The invention is further illustrated with reference to the following examples.

EXAMPLES

Example 1

Preparation of 2,4-bis(4-methyl-1-piperazinyl)-3H-[1,5]benzodiazepine (IV)

3H-[1,5]Benzodiazepine-2,4-diamine (32.50 g, 160 mmol, 86%) was added to a solution of dimethyl sulfoxide (220 ml), toluene (220 ml) and 1-methylpiperazine (165 ml). The mixture was heated for 16 h at 120° C. After cooling the product precipitated. It was filtered off and washed with isopropyl ether (80 ml) to give 40.1 g (74%) of the title compound as off-white needles. The second crop was obtained by adding isopropyl ether (410 ml) to the filtrate. The mixture was allowed to stand overnight at 4° C., the crystallised product was filtered off to give additional 4.25 g (8%) of the title compound. For analytical purposes the product was recrystallised from ethyl acetate.

M.P. 227-228° C. (ethyl acetate). $^1$H-NMR (DMSO-$d_6$) δ=2.21 (s, 6H), 2.35 (m, 8H), 3.02 (broad s, 2H), 3.54 (m, 8H), 6.88 (m, 2H), 7.01 (m, 2H). HRMS calcd. for $C_{15}H_{28}N_6$: 340.2375 found: 340.2387.

Example 2

Preparation of 1-[2,4-bis(4-methyl-1-piperazinyl)-3H-[1,5]benzodiazepin-3-yl]-1-propanol (VI)

A suspension of 2,4-bis(4-methyl-1-piperazinyl)-3H-[1,5] benzodiazepine (17.024 g, 50 mmol) in tetrahydrofuran (200 ml) under constant flow of argon was cooled to −30° C. A solution of lithium diisopropylamide (LDA) (2 M, 37.5 ml, 75 mmol) was added dropwise. Thus obtained dark brown suspension was allowed to warm to −5° C., and then again cooled to −30° C. Propionaldehyde (5.50 ml, 75 mmol) was added during 5 min. The resulting pale brown suspension was allowed to warm to 10° C., while strongly agitated water (250 ml) was added. The solution was transferred to a separating funnel, chloroform (150 ml) was added and the phases were separated. The water phase was extracted with chloroform (2×50 ml). The combined organic phases were dried over anhydrous $Na_2SO_4$ and the solvent was evaporated at reduced pressure. The crude product was suspended in hexane (750 ml), filtered off and washed with hexane (75 ml) to give 18.34 g (92%) of the title compound as an off-white powder. For analytical purposes the product was recrystallised from ethyl acetate.

M.P. 163-166° C. (ethyl acetete). $^1$H-NMR (CDCl$_3$) δ=0.69 (t, 3H), 1.25 (m, 2H), 2.24 (s, 3H), 2.30 (s, 3H), 2.44 (m, 8H), 3.04 (td, 1H), 3.33 (broad s, 1H), 3.57 (m, 8H), 4.51 (d, 1H), 6.98 (m, 2H), 7.10 (m, 1H), 7.22 (m, 1H). HRMS calcd. for $C_{22}H_{34}N_6O$: 398.2794 found: 398.2806.

Example 3

Preparation of 2,4-bis(4-methyl-1-piperazinyl)-3-propylidene-3H-[1,5]benzodiazepine (III)

Method A

A suspension of 2,4-bis(4-methyl-1-piperazinyl)-3H-[1,5] benzodiazepine (1.702 g, 5 mmol) in tetrahydrofuran (20 ml) under constant flow of argon was cooled to −30° C. A solution of lithium diisopropylamide (LDA) (2 M, 3.75 ml, 7.5 mmol) was added dropwise. Thus obtained dark brown suspension was allowed to warm to −5° C. until dissolved and then again cooled to −30° C. Propionaldehyd (0.54 ml, 7.5 mmol) was added during 5 min. The resulting clear yellow solution was allowed to warm to −5° C., triethylamine (5.55 ml, 40 mmol) and pyridine (0.040 ml, 0.5 mmol) were added. A solution of trifluoroacetic anhydride (4.2 ml, 30 mmol) in tetrahydrofuran (6 ml) was added dropwise maintaining the temperature at −5° C. The reaction mixture was stirred for another hour. Methanol (5 ml) and while strongly agitated NaOH (1 M, 35 ml) were added dropwise. The reaction mixture was stirred for four hours while slowly warming to room temperature. The solution was made acidic at ph of 1 and extracted with dichloromethane (3×25 ml). The water phase was made alkalic at a pH of 10 and extracted with diethyl ether (15×25 ml). After each extraction water phase was adjusted to pH of 10. The ether phase was dried over anhydrous $Na_2SO_4$ and ether was evaporated at reduced pressure to give 1, 701 g (89%) of the title compound as a yellow resin.

$^1$H-NMR (CDCl$_3$) δ=0.76 (t, 3H), 1.97 (m, 2H), 2.34 (s, 6H), 2.45 (m, 8H), 3.69 (m, 8H), 5.32 (t, 1H), 6.95 (m, 2H), 7.16 (m, 2H). HRMS calcd. for $C_{22}H_{32}N_6$: 380.2688 found: 380.2697.

Method B

To a suspension of 1-[2,4-bis(4-methyl-1-piperazinyl)-3H-[1,5]benzodiazepin-3-yl]-1-propanol (1.195 g, 3 mmol), triethylamine (2.50 ml, 18 mmol) and pyridine (0.024 ml, 0.3 mmol) in tetrahydrofuran (10 ml) under constant flow of argon, at 0° C., a solution of trifluoroacetic anhydride (1.26 ml, 9 mmol) in tetrahydrofuran (5 ml) was added dropwise. The reaction mixture was stirred for another hour at 0° C. Methanol (5 ml) was added. The solution was allowed to warm to 10° C., while strongly agitated NaOH (1 M, 20 ml) was added dropwise. Dichloromethane (30 ml) was added and the phases were separated. The organic phase was dried over anhydrous $Na_2SO_4$ and the solvent was evaporated at reduced pressure. The crude product was suspended in isopropyl ether (8 ml) and filtered off. The filtrate was evaporated at reduced pressure to give 0.971 g (84%) of the title compound as a yellow resin. The product obtained was characterized using $^1$H-NMR spectroscopy and was found to be identical to the product obtained by method A.

Method C

To a suspension of 1-[2,4-bis(4-methyl-1-piperazinyl)-3H-[1,5]benzodiazepin-3-yl]-1-propanol (19.93 g, 50 mmol) and triethylamine (45 ml, 325 mmol) in dichloromethane (100 ml) under constant flow of argon, at 0° C., a solution of trifluoroacetic anhydride (21 ml, 150 mmol) in dichloromethane (50 ml) was added dropwise. The reaction mixture was stirred for another hour at 0° C. The solution was allowed to warm to room temperature. Methanol (66 ml) and tetrabutylammonium bromide (1.61 g, 5 mmol) were added successively. While strongly agitated NaOH (1 M, 660 ml) was added dropwise. Two phase system was agitated for two hours. The phases were separated and the water phase was extracted with dichloromethane (2×100 ml). The organic phase was dried over anhydrous $Na_2SO_4$ and the solvent was evaporated at reduced pressure. The crude product was suspended in isopropyl ether (150 ml) and filtered off the filtrate was evaporated at reduced pressure to give 14.44 g (76%) of the title compound as a brown resin.

The product obtained was characterised using $^1$H-NMR sprectrosopy and was found to be identical to the product obtained by method A.

Method D

A suspension of 2,4-bis(4-methyl-1-piperazinyl)-3H-[1,5]benzodiazepine (45.396 g, 133.3 mmol) in tetrahydrofuran (560 ml) under constant flow of argon was cooled to −10° C. A solution of lithium diisopropylamide (LDA) (2M, 100 ml, 200 mmol) was added over a period of 20 min, maintaining the temperature at −10° C. The obtained deep red solution was stirred for 30 min. Propionaldehyde (14.6 ml, 200 mmol) was added dropwise. Triethylamine (148 ml, 1.067 mol) and pyridine (0.54 ml, 6.7 mmol) were added successively. Trifluoroacetacetic anhydride (93.1 ml, 667 mmol) was added over a period of 50 min, maintaining the temperature at −10° C. The reaction mixture was stirred for 1 h and allowed to warm to −5° C. Methanol (213 ml) and while strongly agitated NaOH (5M, 200 ml, 1.000 mol) were added maintaining the temperature at −5° C. The reaction mixture was allowed to warm to room temperature and stirred over night. The solution was made acidic with 5M HCl to a pH of 3.5. Two phases were formed and the lower layer was extracted with 600 ml and twice with 100 ml of dichloromethane. The aqueous phase was treated with brine (200 ml) and toluene (400 ml) and made alkaline with 5M NaOH to a pH of 10. The phases were separated and the aqueous phase was extracted with toluene (2×200 ml). Combined toluene phases were dried over anhydrous $Na_2SO_4$ and the solvent was evaporated at reduced pressure to give 48.38 g (95%) of the title compound as an amber resin. The product obtained was characterised using $^1$H-NMR spectroscopy and was found to be identical to the product obtained by method A.

Example 4

Preparation of Olanzapine

A suspension of 2,4-bis(4-methyl-1-piperazinyl)-3-propylidene-3H-[1,5]benzodiazepine (11.90 g, 31.3 mmol), sulphur (20.07 g, 626 mmol) and triethyl amine (4.34 ml, 31.3 mmol) in dimethyl sulfoxide (100 ml) and 1-propanol (100 ml) was heated at 100° C. for five days. The resulting black suspension was cooled and filtered off and the filtrate was evaporated at reduced pressure to obtain a viscous black oil. Dichloromethane (600 ml) and HCl (0.2 M, 600 ml) were added and the phases were separated. The organic phase was extracted again with HCl (0.5 M, 100 ml). The combined water phases were made alkalic at a pH of 9 to 10. Dark brown precipitate was filtered off. Dichloromethane (250 ml) was added to the filtrate. The phases were separated and the water phase was extracted with dichloromethane (2×60 ml). The organic phase was dried over anhydrous $Na_2SO_4$ and the solvent was evaporated at reduced pressure. The black oil was combined with precipitate and purified by chromatography on silica gel, eluted with ethyl acetate/triethylamine 50/1 to obtain 1.195 g (12%) of the title product.

Example 5

Preparation of Olanzapine

Method A

To a 0.118 M solution of 2,4-bis(4-methyl-1-piperazinyl)-3-propylidene-3H-[1,5]benzodiazepine in benzonitrile (50 ml, 5.90 mmol) quinolinium p-toluenesulfonate (3.01 g, 10 mmol) and sulphur (0.64 g, 20 mmol) were added. The reaction mixture was stirred at 140° C. for 13.5 h, cooled to 110° C. and concentrated (78-80° C./24-30 mbar) to an oily residue. The residue was dissolved in dichloromethane (35 ml), water (30 ml) was added and the mixture was made acidic with 2M HCl to a pH of 0.9. The phases were separated and the aqueous phase was extracted with dichloromethane (3×30 ml). The aqueous phase was made alkaline with 15% NaOH to a pH of 7.4 and extracted with dichloromethane (2×30 ml). The combined dichloromethane phases were dried over anhydrous $Na_2SO_4$ and the solvent was evaporated at reduced pressure to give 1.91 g of crude Olanzapine. It contained 4.1 mmol (69.5% yield) of Olanzapine.

Method B

To a 0.118 M solution of 2,4-bis(4-methyl-1-piperazinyl)-3-propylidene-3H-[1,5]benzodiazepine in benzonitrile (50 ml, 5.90 mmol) pyridinium p-toluenesulfonate (2.51 g, 10 mmol) and sulphur (0.64 g, 20 mmol) were added. The reaction mixture was stirred at 140° C. for 13.5 h, cooled to 110° C. and concentrated (78-80° C./24-30 mbar) to an oily residue. The residue was dissolved in dichloromethane (35 ml), water (30 ml) was added and the mixture was made acidic with 2M HCl to a pH of 0.64. The phases were separated and the aqueous phase was extracted with dichloromethane (2×30 ml). The dichloromethane phases were reextracted with diluted HCl (2×30 ml). The combined aqueous phases were made alkaline with 15% NaOH to a pH of 7.9 and extracted with dichloromethane (1×50 ml, 2×30 ml). The organic phase was dried over anhydrous $Na_2SO_4$. The solvent was evaporated at reduced pressure to give 1.534 g of crude Olanzapine. It contained 3.93 mmol (66.6% yield) of Olanzapine.

Method C

To a 0.118 M solution of 2,4-bis(4-methyl-1-piperazinyl)-3-propylidene-3H-[1,5]benzodiazepine in benzonitrile (10 ml, 1.18 mmol) 1-methylimidazolinium p-toluenesulfonate (0.51 g, 2 mmol) and sulphur (0.128 g, 4 mmol) were added. The reaction mixture was stirred at 140° C. for 10 h, then it was cooled to room temperature and left over night. The reaction mixture was heated to 110° C. and concentrated (78-80° C./24-30 mbar) to an oily residue. The residue was dissolved in dichloromethane (10 ml), water (10 ml) was added and the mixture was made acidic with 2M HCl to a pH of 0.9. The phases were separated and the aqueous phase was extracted with dichloromethane (3×6 ml). The aqueous phase was made alkaline with 15% NaOH to a pH of 8.5 and extracted with dichloromethane (6×6 ml). The combined dichloromethane phases were dried over anhydrous $Na_2SO_4$ and the solvent was evaporated at reduced pressure to give 0.313 g of crude Olanzapine. It contained 0.64 mmol (54.2% yield) of Olanzapine.

Method D

To a 0.118 M solution of 2,4-bis(4-methyl-1-piperazinyl)-3-pro-pylidene-3H-[1,5]benzodiazepine in benzonitrile (10 ml, 1.18 mmol) p-toluenesulfonic acid monohydrate (0.380 g, 2 mmol) and sulphur (0.128 g, 4 mmol) were added. The reaction mixture was stirred at 140° C. for 9 h, cooled to 110° C. and concentrated (78-80° C./24-30 mbar) to an oily residue. The residue was dissolved in dichloromethane (15 ml), water (10 ml) was added and the mixture was made acidic with 2M HCl to a pH of 1.0. The phases were separated and the aqueous phase was extracted with dichloromethane (2×10 ml). The dichloromethane phases were reextracted with diluted HCl (10 ml). The combined aqueous phases were made alkaline with 15% NaSO to a pH of 7.9 and extracted with dichloromethane (3×30 ml). The organic phase was dried over anhydrous $Na_2SO_4$. The solvent was evaporated at reduced pressure to give 0.252 g of crude Olanzapine. It contained 0.61 mol (51.7% yield) of Olanzapine.

The invention claimed is:

1. Process for the manufacture of Olanzapine of the following formula I or a salt thereof:

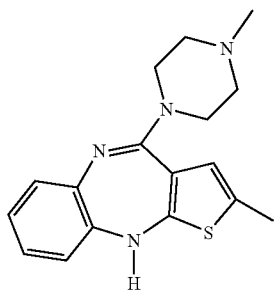

I by converting a compound of the following formula II or a salt thereof

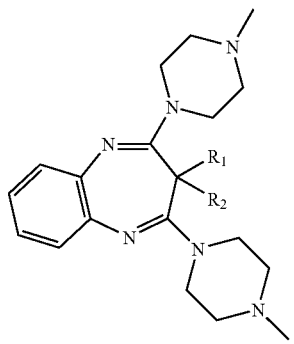

II wherein
(i) $R_1$ and $R_2$ together form =CH—$CH_2$—$CH_3$, or
(ii) $R_1$ and $R_2$ are both H, or
(iii) $R_1$ is H and $R_2$ is —CH($R_3$)—$CH_2$—$CH_3$, wherein $R_3$ is a leaving group that can be eliminated together with $R_1$ to result in $R_1$ and $R_2$ together forming =CH—$CH_2$—$CH_3$,
to give Olanzapine or a salt thereof.

2. Process according to claim 1, wherein the leaving group $R_3$ is —$OR_4$, $R_4$ is selected from the group consisting of H, acyl, and sulfonyl.

3. Process according to claim 2, wherein $R_4$ is H.

4. Process according to claim 2, wherein $R_4$ is trifluoroacetyl or methane sulfonyl.

5. Process according to claim 1, wherein $R_1$ and $R_2$ together form =CH—$CH_2$—$CH_3$ and the conversion is performed by reacting the compound of formula II with a source of sulfur.

6. The process according to claim 1, wherein the compound of formula II is benzodiazepine of the following formula IV:

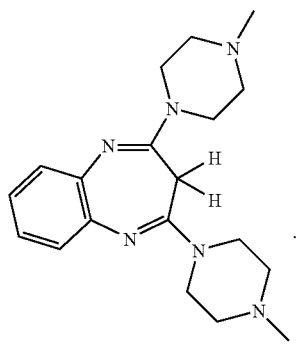

IV

7. The process according to claim 1, wherein the compound of formula II is benzodiazepine-propanol of the following formula VI:

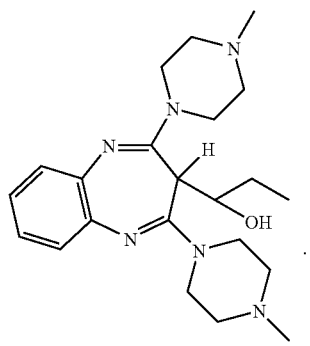

VI

8. The process according to claim 1, wherein the compound of formula II is benzodiazepine-ester of the following formula VII:

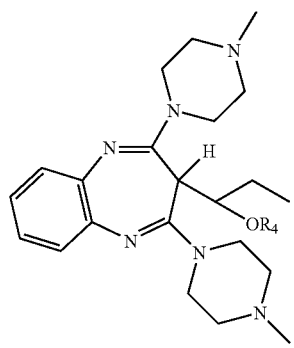

VII wherein $R_4$ is selected from the group consisting of acyl and sulfonyl.

9. A compound of the following formula

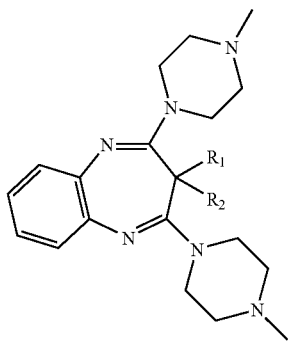

or salts thereof
wherein
(i) $R_1$ and $R_2$ together form $=CH-CH_2-CH_3$, or
(ii) $R_1$ and $R_2$ are both H, or
(iii) $R_1$ is H and $R_2$ is $-CH(R_3)-CH_2-CH_3$, wherein $R_3$ is $-OR_4$, $R_4$ is selected from the group consisting of hydrogen, acyl and sulfonyl.

10. The compound of claim 9 wherein $R_1$ is H and $R_2$ is $-CH(R_3)-CH_2-CH_3$, wherein $R_3$ is $-OR_4$ and $R_4$ is trifluoroacetyl or methane sulfonyl.

11. The compound according to claim 9, which is a propylidene-benzodiazepine of the following formula III:

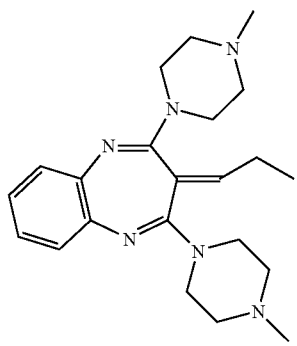

12. The compound according to claim 9, which is benzodiazepine of the following formula IV:

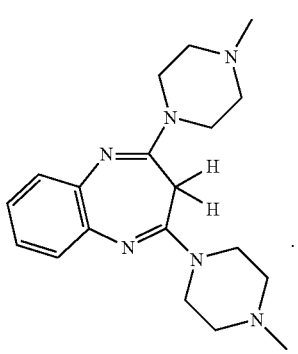

13. The compound according to claim 9, which is benzodiazepine-propanol of the following formula VI:

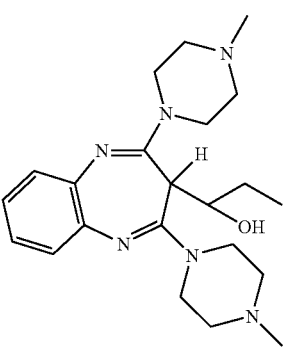

14. The process of claim 8 wherein $R_4$ is trifluoroacetyl or methane sulfonyl.

* * * * *